United States Patent
Waters

(10) Patent No.: US 7,422,023 B1
(45) Date of Patent: Sep. 9, 2008

(54) TISSUE VALVE CLEANSING APPARATUS

(76) Inventor: Raymond S. Waters, 375 Coldeway Dr., H-14, Punta Gorda, FL (US) 33950

(*) Notice: Subject to any disclaimer, the term of this patent is extended or adjusted under 35 U.S.C. 154(b) by 595 days.

(21) Appl. No.: 11/144,416

(22) Filed: Jun. 6, 2005

(51) Int. Cl.
B08B 3/04 (2006.01)
B08B 13/00 (2006.01)

(52) U.S. Cl. ............... 134/140; 134/157; 134/160; 366/288; 366/331

(58) Field of Classification Search ............. 366/197, 366/241, 276–278, 288, 331; 134/140, 157, 134/160
See application file for complete search history.

(56) References Cited

U.S. PATENT DOCUMENTS

| | | | |
|---|---|---|---|
| 1,192,426 A * | 7/1916 | Hudson | 416/122 |
| 1,350,171 A * | 8/1920 | Niederberger | 366/288 |
| 1,879,441 A * | 9/1932 | Olson | 134/140 |
| 2,091,402 A * | 8/1937 | Waterworth | 68/133 |
| 2,184,020 A * | 12/1939 | Repasy | 134/77 |
| 4,881,562 A | 11/1989 | Wright | |
| 5,476,321 A | 12/1995 | McNaughton | |
| 5,533,805 A | 7/1996 | Mandel | |
| 5,613,425 A | 3/1997 | Krznaric | |
| 5,836,687 A | 11/1998 | Khalid | |
| 6,264,358 B1 | 7/2001 | Eisaman | |
| 6,439,760 B1 * | 8/2002 | Langeloh et al. | 366/206 |

* cited by examiner

Primary Examiner—David L Sorkin

(57) ABSTRACT

The apparatus includes a housing having a centrally disposed longitudinal axis situated along a horizontal plane during operating conditions. The housing further has a monolithically formed flange portion extending orthogonally therefrom. The flange portion has a plurality of slots formed therein. A plurality of coextensive and independently pivotal leg members directly conjoined to the housing and the flange portion in such a manner that the apparatus can conveniently be supported at an elevated position above a ground surface during operating conditions. A rectilinear bracket has opposed end portions pivotally and directly connected to the flange portion and one of the leg members respectively. A mechanism is included for agitating a tissue valve in a saline solution.

18 Claims, 4 Drawing Sheets

TISSUE VALVE CLEANSING APPARATUS

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to surgical cleaning apparatuses and, more particularly, to a tissue valve cleansing apparatus.

2. Prior Art

Modern surgical procedures, especially those involving implantation, require extensive preparation and sanitation of the materials involved in said procedure. Such preparation demands attention to prevent infection or other complications from arising either during or after the procedure. Currently, preparation and sanitation of tissue valves requires the attention of a user to manually wash the valve in a saline solution before implantation. This method is tedious, inefficient, and time consuming, therefore, a need for a valve washing apparatus has arisen.

Some examples of this approach consist of intricate and complex apparatuses utilizing a myriad of tubing and sensors which render the prior art bulky, cumbersome, expensive, and difficult to operate.

Accordingly, a need remains for a tissue valve cleansing apparatus in order to overcome the above-noted shortcomings. The present invention satisfies such a need by providing a valve cleansing apparatus that is portable, compact, efficient, easy to set up, practical and inexpensive to manufacture. The tissue valve cleansing apparatus appeals to surgeons, hospitals, and medical clinics as well as other medical professionals and institutions.

BRIEF SUMMARY OF THE INVENTION

In view of the foregoing background, it is therefore an object of the present invention to provide an apparatus for cleaning tissue valves. These and other objects, features, and advantages of the invention are provided by an apparatus for automatically cleaning and preparing a tissue valve for surgical insertion.

The apparatus includes a housing having a centrally disposed longitudinal axis situated along a horizontal plane during operating conditions. Such a housing further has a monolithically formed flange portion extending orthogonally therefrom. The flange portion has a plurality of slots formed therein.

A plurality of coextensive and independently pivotal leg members are directly conjoined to the housing and the flange portion in such a manner that the apparatus can conveniently be supported at an elevated position above a ground surface during operating conditions. A rectilinear bracket has opposed end portions pivotally and directly connected to the flange portion and one of the leg members respectively wherein another of the leg members is pivotally and directly connected to the housing. Such a bracket is pivotal 90 degrees so that the apparatus can be readily stored.

A mechanism is included for agitating a tissue valve in a saline solution. Such an agitating mechanism preferably includes an annular flywheel disposed conveniently within the housing. The agitating mechanism may have upper and lower agitator arms having respective linear slots formed medially therein and extending along a partial length thereof. The upper and lower agitator arms have opposed end portions with one of the end portions directly conjoined to the flywheel. A clamp is directly conjoined to another of the end portions of the upper and the lower agitator arms. The clamp is resiliently adaptable between open and closed positions for advantageously maintaining the tissue valve at a substantially stable position during operating conditions.

A motor includes an output shaft extending orthogonally therefrom. The output shaft includes a gear directly conjoined thereto. Such a gear engages the flywheel and causes the flywheel to rotate in a corresponding direction when the motor rotates the output shaft about an axis obliquely offset from the longitudinal axis. An annular disc may be statically housed within the flange portion and directly interfitted within the slots of the upper and lower agitator arms. The discs linearly glide along corresponding lengths of the slots as the agitator arms are elliptically biased during operating conditions. The agitator arms are caused to oscillate along an elliptical path when the flywheel is rotated such that the tissue valve can be concentrically agitated within a bowl of saline solution.

A power source is preferably disposed within the housing and electrically coupled to the motor. A switch is preferably included for toggling the motor between on and off positions.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

Figure 1:
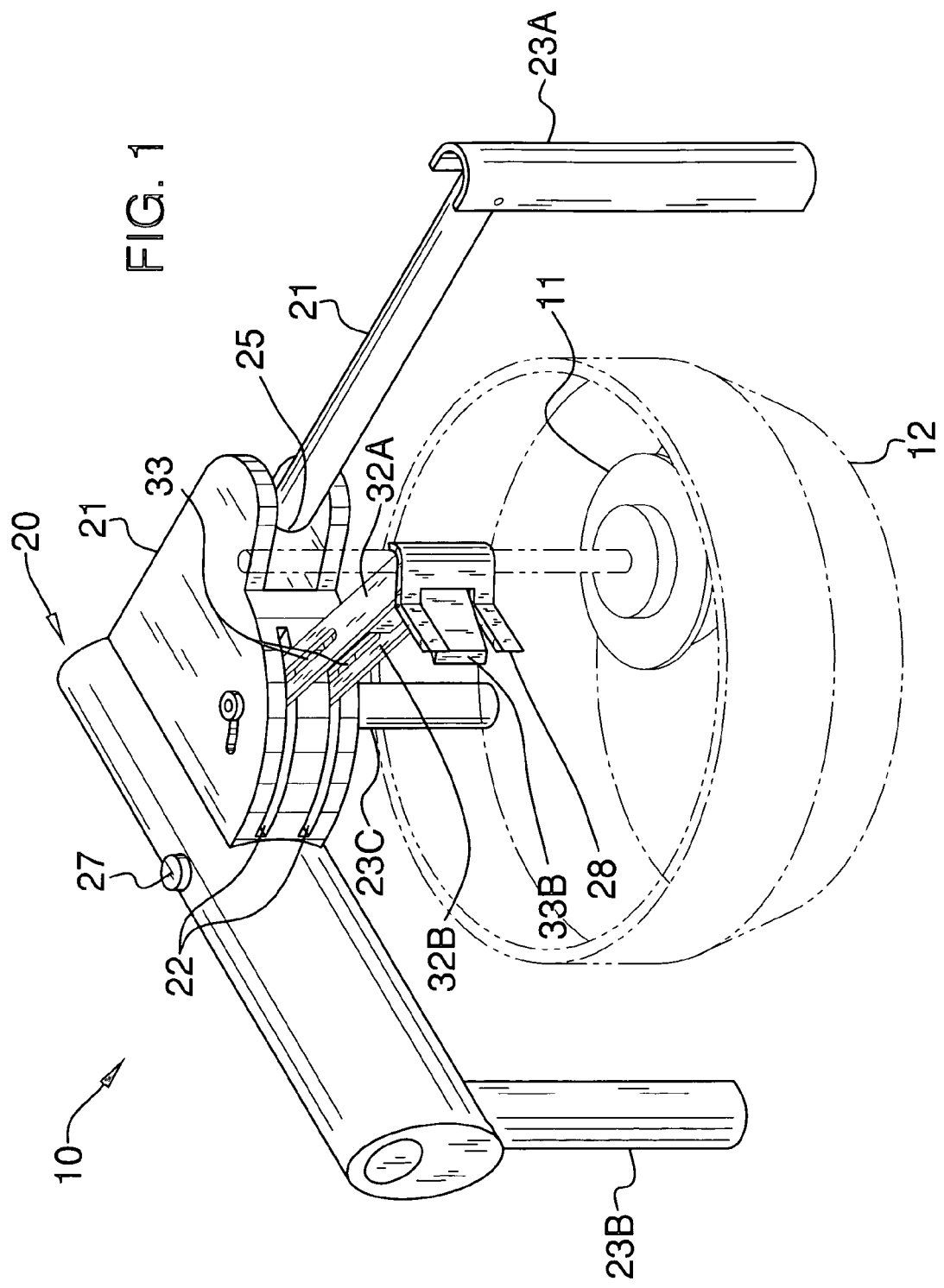
FIG. 1 is a perspective view showing an apparatus for cleaning and preparing a tissue valve for surgical insertion, in accordance with the present invention.
Figure 2:
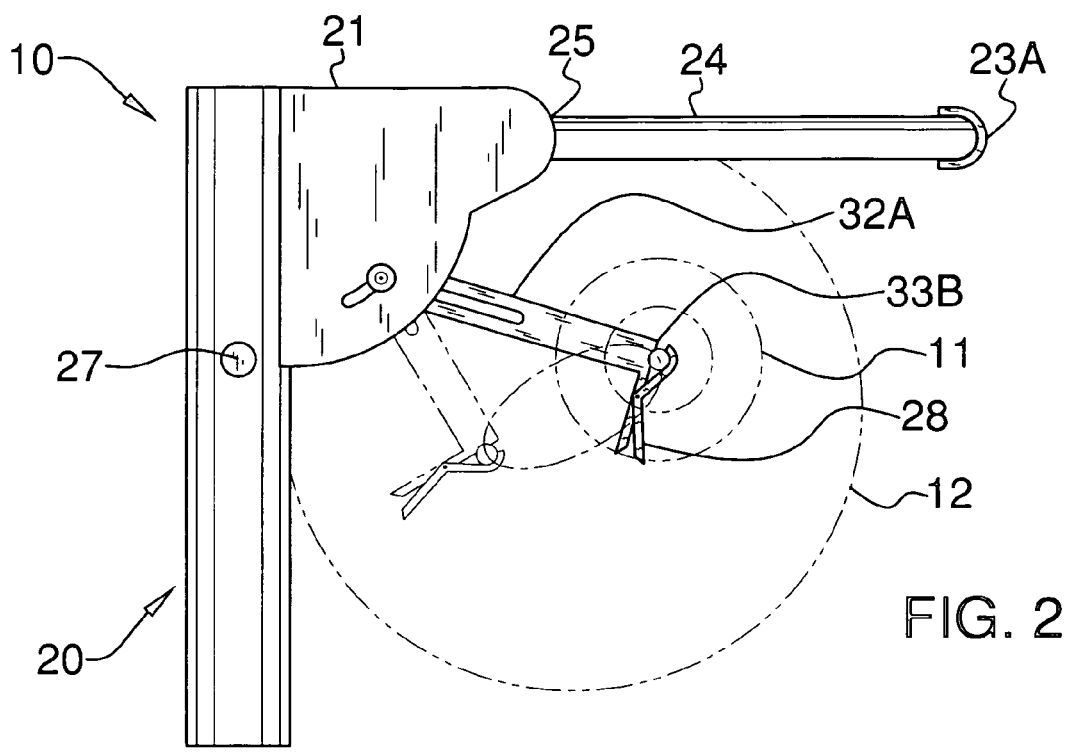
FIG. 2 is a top plan view of the apparatus shown in FIG. 1, illustrating the elliptical motion of the agitator arms during operating conditions.

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The apparatus of this invention is referred to generally in FIGS. 1-6 by the reference numeral 10 and is intended to provide a tissue valve cleansing apparatus. It should be understood that the apparatus 10 may be used to sanitize many different types of objects and should not be limited in use to only cleansing or sanitizing surgical implements.

Figure 4:
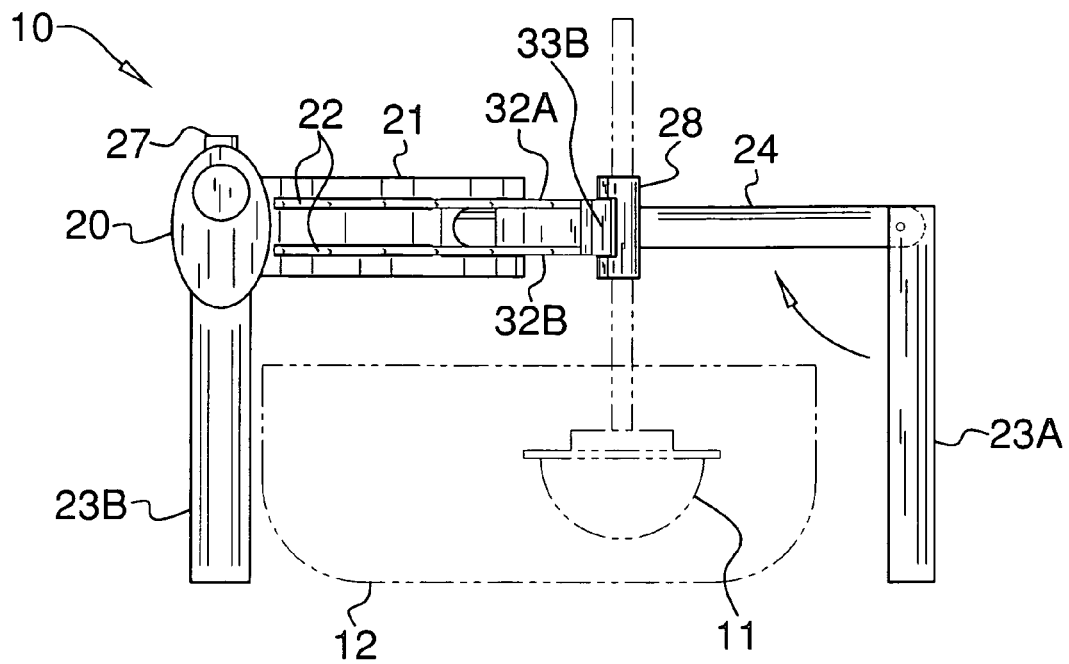
FIG. 4 is a side-elevational view of the apparatus shown in FIG. 1.
Figure 5:
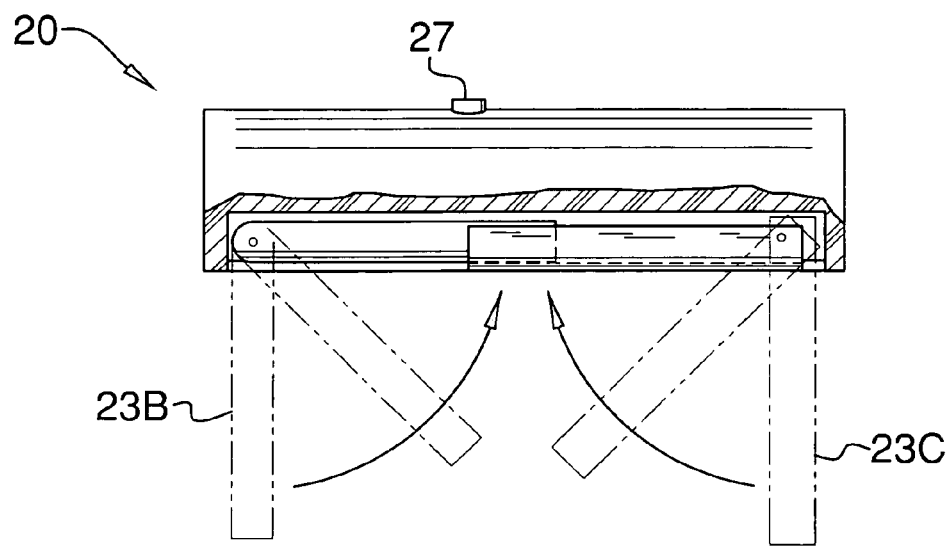
FIG. 5 is a partially exposed side-elevation view of the apparatus as shown in FIG. 1, illustrating pivoting action of the leg members.
Figure 6:
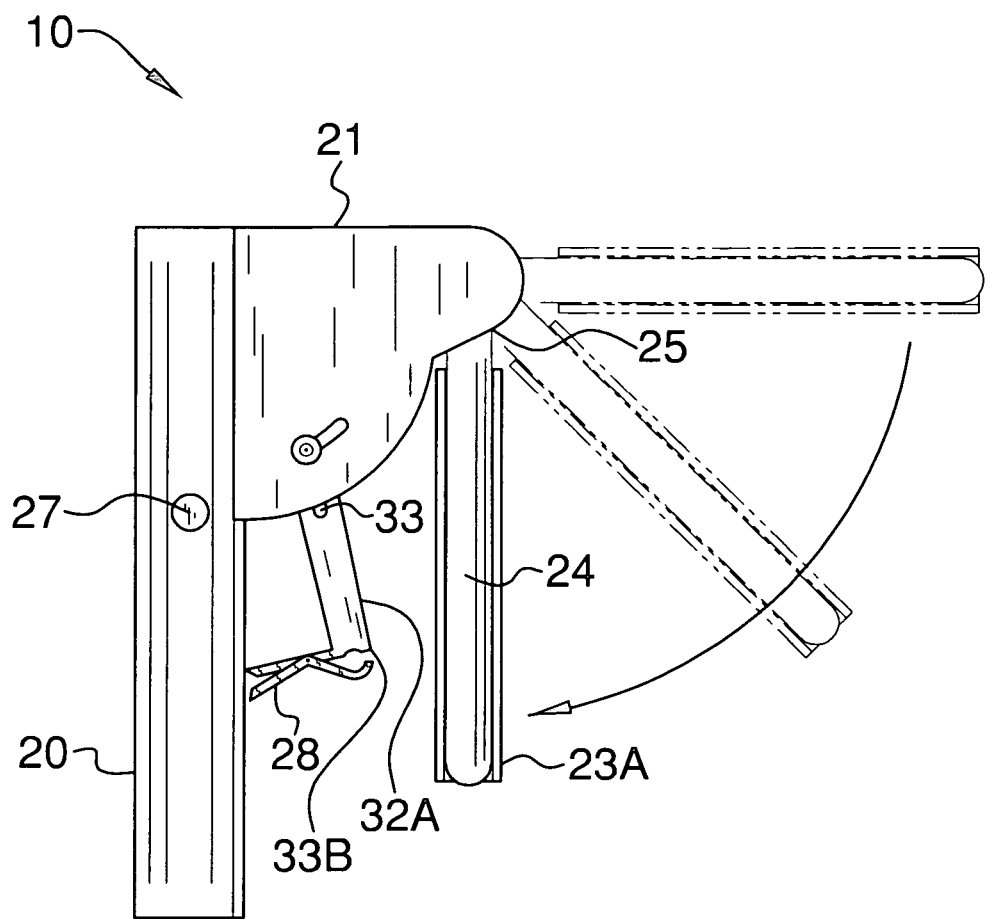
FIG. 6 is a top plan view of the apparatus shown in FIG. 1, illustrating the pivoting action of the bracket.

Initially referring to FIGS. 1 and 4, the apparatus 10 includes a housing 20 having a centrally disposed longitudinal axis situated along a horizontal plane during operating conditions. Such a housing 20 further has a monolithically formed flange portion 21 extending orthogonally therefrom. The flange portion 21 may have a plurality of slots 22 formed therein.

Referring to FIGS. 1-6, a plurality of coextensive and independently pivotal leg members 23B, 23C are directly conjoined, with no intervening elements, to the housing 20 and the flange portion 21 in such a manner that the apparatus 10 can conveniently be supported at an elevated position above a ground surface during operating conditions. A rectilinear bracket 24 has opposed end portions 25 pivotally and directly connected, with no intervening elements, to the flange portion 21 and one of the leg members 23A respectively, wherein another of the leg members 23B,23C may be pivotally and directly connected, with no intervening elements, to the housing 20. Such a bracket 24 is pivotal 90 degrees so that the apparatus 10 can readily stored. This is essential for allowing ease of transportation and quick set up of the apparatus 10 by the user.

Figure 3:
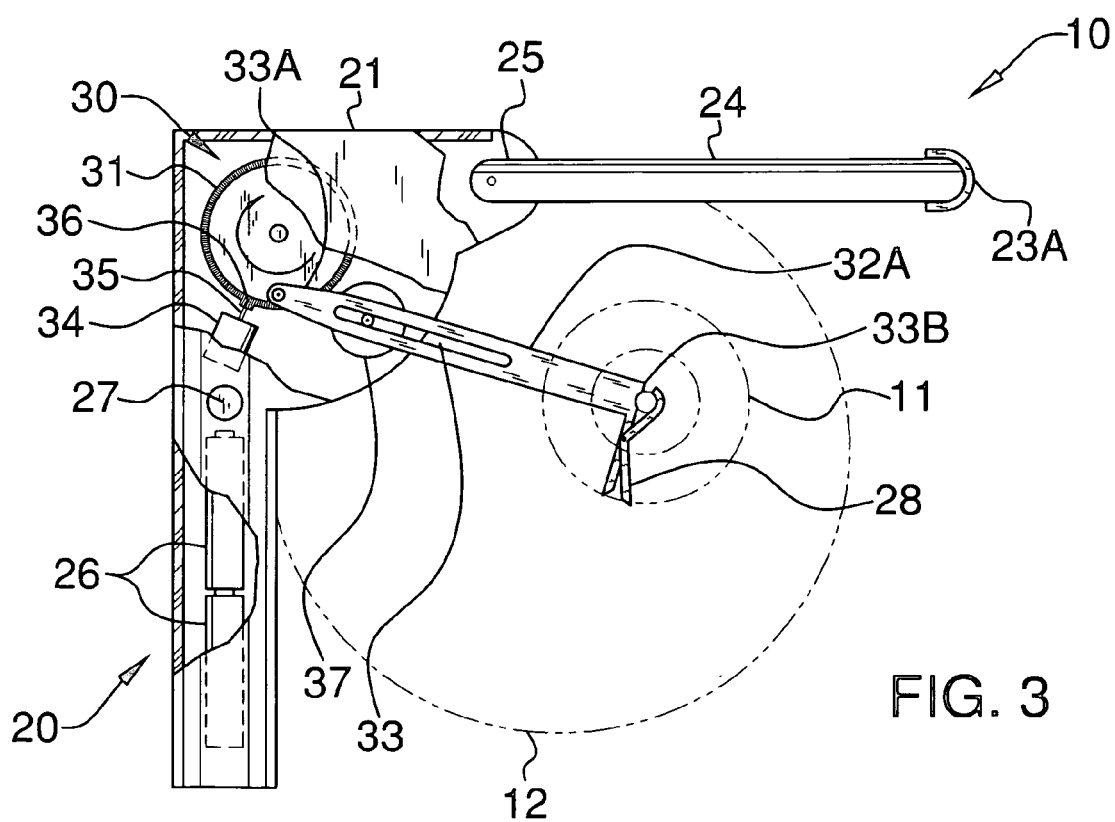
FIG. 3 is a partially exposed top plan view of the apparatus shown in FIG. 1.

Referring to FIGS. 1 and 3, a mechanism 30 is included for agitating a tissue valve 11 in a saline solution 12. Such an agitating mechanism 30 includes an annular flywheel 31 disposed conveniently within the housing 20. The agitating mechanism 30 has upper 32A and lower 32B agitator arms having respective linear slots 33 formed medially therein and extending along a partial length thereof. The upper 32A and lower 32B agitator arms have opposed end portions 33 with one of the end portions 33A directly conjoined, with no intervening elements, to the flywheel 31. A clamp 28 is directly conjoined to another of the end portions 33B of the upper 32A and the lower 32B agitator arms. The clamp 28 is resiliently adaptable between open and closed positions for advantageously maintaining the tissue valve 11 at a substantially stable position during operating conditions.

Referring again to FIGS. 1 and 3, a motor 34 includes an output shaft 35 extending orthogonally therefrom. The output shaft 35 includes a gear 36 directly conjoined thereto, with no intervening elements. Such a gear 36 engages the flywheel 31 and causes the flywheel 31 to rotate in a corresponding direction when the motor 34 rotates the output shaft 35 about an axis obliquely offset from the longitudinal axis. A power source 26 is disposed within the housing 20 and electrically coupled to the motor 26. A switch 27 is included for toggling the motor 26 between on and off positions.

A plurality of annular discs 37 may be statically housed within the flange portion 21 and directly interfitted, with no intervening elements, within the slots 33 of the upper 32A and lower 32B agitator arms. The discs 37 linearly glide along corresponding lengths of the slots 33 as the agitator arms are elliptically biased during operating conditions. The agitator arms 32 are caused to oscillate along an elliptical path when the flywheel 31 is rotated such that the tissue valve 11 can be concentrically agitated within a bowl of saline solution 12. Such a feature is critical to the operation of the apparatus 10 for ensuring proper cleansing of the surgical valve.

The automatic agitation of the apparatus 10 allows the user to quickly and effectively prepare the surgical valve 11 for insertion without requiring a user's constant attention, thereby allowing for a much safer and more efficient procedure. The replacement of a manual procedure with an automated one also allows the user to focus on other tasks at hand, thus increasing the overall quality of the procedure.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A tissue valve cleansing apparatus for washing tissue valves prior to surgical insertion, said apparatus comprising:

a housing having a centrally disposed longitudinal axis situated along a horizontal plane during operating conditions, said housing further having a monolithically formed flange portion extending orthogonally therefrom, said flange portion having a plurality of slots formed therein;

a plurality of leg members directly conjoined to said housing and said flange portion in such a manner that said apparatus can be supported at an elevated position above a ground surface during operating conditions;

a rectilinear bracket having opposed end portions pivotally and directly connected to said flange portion and one said leg members respectively; and means for agitating a tissue valve in a saline solution.

2. The apparatus of claim 1, wherein another said leg members is pivotally and directly connected to said housing.

3. The apparatus of claim 1, wherein said agitating means comprises:

an annular flywheel disposed within said housing;

upper and lower agitator arms having respective linear slots formed medially therein and extending along a partial length thereof, said upper and lower agitator arms having opposed end portions, one said end portions being directly conjoined to said flywheel;

a clamp directly conjoined to another said end portions of said upper and said lower agitator arms, said clamp being resiliently adaptable between open and closed positions for maintaining the tissue valve at a substantially stable position during operating conditions;

a motor including an output shaft extending orthogonally therefrom, said output shaft including a gear directly conjoined thereto, said gear engaging said flywheel and causing said flywheel to rotate in a corresponding direction when said motor rotates said output shaft about an axis obliquely offset from the longitudinal axis;

wherein said agitator arms are caused to oscillate along an elliptical path when said fly wheel is rotated such that the tissue valve can be concentrically agitated within a bowl of saline solution; and a power source disposed within said housing and electrically coupled to said motor.

4. The apparatus of claim 3, wherein said agitating means further comprises: a switch for toggling said motor between on and off positions.

5. The apparatus of claim 3, wherein said agitating means further comprises: an annular disc statically housed within said flange portion and directly interfitted within the slots of said upper and lower agitator arms, said discs linearly gliding along corresponding lengths of the slots as said agitator arms are elliptically biased during operating conditions.

6. The apparatus of claim 1, wherein said bracket is pivotal 90 degrees such that said apparatus can readily stored.

7. A tissue valve cleansing apparatus for washing tissue valves prior to surgical insertion, said apparatus comprising:

a housing having a centrally disposed longitudinal axis situated along a horizontal plane during operating conditions, said housing further having a monolithically formed flange portion extending orthogonally therefrom, said flange portion having a plurality of slots formed therein;

a plurality of coextensive leg members directly conjoined to said housing and said flange portion in such a manner that said apparatus can be supported at an elevated position above a ground surface during operating conditions;

a rectilinear bracket having opposed end portions pivotally and directly connected to said flange portion and one said leg members respectively; and means for agitating a tissue valve in a saline solution.

8. The apparatus of claim 7, wherein another said leg members is pivotally and directly connected to said housing.

9. The apparatus of claim 7, wherein said agitating means comprises:

an annular flywheel disposed within said housing;

upper and lower agitator arms having respective linear slots formed medially therein and extending along a partial length thereof, said upper and lower agitator arms having opposed end portions, one said end portions being directly conjoined to said flywheel;

a clamp directly conjoined to another said end portions of said upper and said lower agitator arms, said clamp being resiliently adaptable between open and closed positions for maintaining the tissue valve at a substantially stable position during operating conditions;

a motor including an output shaft extending orthogonally therefrom, said output shaft including a gear directly conjoined thereto, said gear engaging said flywheel and causing said flywheel to rotate in a corresponding direction when said motor rotates said output shaft about an axis obliquely offset from the longitudinal axis;

wherein said agitator arms are caused to oscillate along an elliptical path when said fly wheel is rotated such that the tissue valve can be concentrically agitated within a bowl of saline solution; and a power source disposed within said housing and electrically coupled to said motor.

10. The apparatus of claim 9, wherein said agitating means further comprises: a switch for toggling said motor between on and off positions.

11. The apparatus of claim 9, wherein said agitating means further comprises: an annular disc statically housed within said flange portion and directly interfitted within the slots of said upper and lower agitator arms, said discs linearly gliding along corresponding lengths of the slots as said agitator arms are elliptically biased during operating conditions.

12. The apparatus of claim 7, wherein said bracket is pivotal 90 degrees such that said apparatus can readily stored.

13. A tissue valve cleansing apparatus for washing tissue valves prior to surgical insertion, said apparatus comprising;

a housing having a centrally disposed longitudinal axis situated along a horizontal plane during operating conditions, said housing further having a monolithically formed flange portion extending orthogonally therefrom, said flange portion having a plurality of slots formed therein;

a plurality of coextensive and independently pivotal leg members directly conjoined to said housing and said flange portion in such a manner that said apparatus can be supported at an elevated position above a ground surface during operating conditions;

a rectilinear bracket having opposed end portions pivotally and directly connected to said flange portion and one said leg members respectively; and means for agitating a tissue valve in a saline solution.

14. The apparatus of claim 13, wherein another said leg members is pivotally and directly connected to said housing.

15. The apparatus of claim 13, wherein said agitating means comprises:

an annular flywheel disposed within said housing;

upper and lower agitator arms having respective linear slots formed medially therein and extending along a partial length thereof, said upper and lower agitator arms having opposed end portions, one said end portions being directly conjoined to said flywheel;

a clamp directly conjoined to another said end portions of said upper and said lower agitator arms, said clamp being resiliently adaptable between open and closed positions for maintaining the tissue valve at a substantially stable position during operating conditions;

a motor including an output shaft extending orthogonally therefrom, said output shaft including a gear directly conjoined thereto, said gear engaging said flywheel and causing said flywheel to rotate in a corresponding direction when said motor rotates said output shaft about an axis obliquely offset from the longitudinal axis;

wherein said agitator arms are caused to oscillate along an elliptical path when said fly wheel is rotated such that the tissue valve can be concentrically agitated within a bowl of saline solution; and a power source disposed within said housing and electrically coupled to said motor.

16. The apparatus of claim 15, wherein said agitating means further comprises: a switch for toggling said motor between on and off positions.

17. The apparatus of claim 15, wherein said agitating means further comprises: an annular disc statically housed within said flange portion and directly interfitted within the slots of said upper and lower agitator arms, said discs linearly gliding along corresponding lengths of the slots as said agitator arms are elliptically biased during operating conditions.

18. The apparatus of claim 13, wherein said bracket is pivotal 90 degrees such that said apparatus can readily stored.

* * * * *